United States Patent
Goto et al.

(10) Patent No.: US 9,975,308 B2
(45) Date of Patent: *May 22, 2018

(54) GLASS/RESIN COMPOSITE STRUCTURE AND METHOD FOR MANUFACTURING SAME

(71) Applicant: HITACHI HIGH-TECHNOLOGIES CORPORATION, Tokyo (JP)

(72) Inventors: Yusuke Goto, Tokyo (JP); Masao Kamahori, Tokyo (JP); Hiroshi Sasaki, Tokyo (JP); Kiyotoshi Mori, Tokyo (JP); Hideyuki Akiyama, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 253 days.

This patent is subject to a terminal disclaimer.

(21) Appl. No.: 14/646,522

(22) PCT Filed: Nov. 1, 2013

(86) PCT No.: PCT/JP2013/079754
§ 371 (c)(1),
(2) Date: May 21, 2015

(87) PCT Pub. No.: WO2014/087774
PCT Pub. Date: Jun. 12, 2014

(65) Prior Publication Data
US 2015/0314550 A1    Nov. 5, 2015

(30) Foreign Application Priority Data

Dec. 7, 2012 (JP) .................................. 2012-268421

(51) Int. Cl.
*B32B 1/08* (2006.01)
*B29C 65/48* (2006.01)
(Continued)

(52) U.S. Cl.
CPC ................ *B32B 1/08* (2013.01); *B01L 3/561* (2013.01); *B29C 65/46* (2013.01);
(Continued)

(58) Field of Classification Search
None
See application file for complete search history.

(56) References Cited

U.S. PATENT DOCUMENTS 4,794,049 A * 12/1988 Takahashi ............. E21B 17/003
138/145
6,825,249 B1    11/2004 Takeda et al.
(Continued)

FOREIGN PATENT DOCUMENTS

CN    101356441 A    1/2009
JP    2001-176895 A    6/2001
(Continued)

OTHER PUBLICATIONS

Chinese Office Action received in corresponding Chinese Application No. 201380062144.3 dated Dec. 30, 2016.

*Primary Examiner* — David Sample
(74) *Attorney, Agent, or Firm* — Mattingly & Malur, PC

(57) ABSTRACT

A composite structure with high pressure resistance that is suitable for a flow channel is produced by reducing the number of components while maintaining the excellent chemical resistance and high stress tolerance inherent to a glass substrate and a resin substrate. A glass substrate surface is modified with a hydrolyzable silicon compound, and the glass substrate is brought into contact with the resin substrate. Subsequently, the contact surface between the glass substrate and the resin substrate is heated to a temperature from the glass transition temperature to the pyrolysis temperature of the resin substrate, eliminating gaps between the glass substrate and the resin substrate to bring them into close contact with each other, and causing chemi-
(Continued)

cal binding or anchor effects between the glass substrate and the resin substrate via the hydrolyzable silicon compound. Thus, the glass substrate and the resin substrate are firmly fixed to each other.

12 Claims, 18 Drawing Sheets

(51) Int. Cl.
| | |
|---|---|
| B01L 3/00 | (2006.01) |
| B32B 7/12 | (2006.01) |
| B32B 27/28 | (2006.01) |
| B29C 65/46 | (2006.01) |
| B32B 17/06 | (2006.01) |
| C09J 5/06 | (2006.01) |
| G01N 21/05 | (2006.01) |
| B32B 27/34 | (2006.01) |
| B32B 27/36 | (2006.01) |
| B29K 71/00 | (2006.01) |
| B29L 23/00 | (2006.01) |
| B29L 31/00 | (2006.01) |

(52) U.S. Cl.
CPC ........... *B29C 65/4895* (2013.01); *B32B 7/12* (2013.01); *B32B 17/064* (2013.01); *B32B 27/281* (2013.01); *B32B 27/285* (2013.01); *B32B 27/286* (2013.01); *B32B 27/288* (2013.01); *B32B 27/34* (2013.01); *B32B 27/365* (2013.01); *C09J 5/06* (2013.01); *G01N 21/05* (2013.01); *B01L 2300/12* (2013.01); *B29K 2071/00* (2013.01); *B29K 2995/0026* (2013.01); *B29K 2995/0058* (2013.01); *B29K 2995/0077* (2013.01); *B29L 2023/22* (2013.01); *B29L 2031/752* (2013.01); *B32B 2255/20* (2013.01); *B32B 2597/00* (2013.01); *C09J 2400/143* (2013.01); *C09J 2400/226* (2013.01); *Y10T 428/1321* (2015.01)

(56) References Cited

U.S. PATENT DOCUMENTS

| | | | |
|---|---|---|---|
| 9,658,153 B2 * | 5/2017 | Goto | G01N 30/74 |
| 2009/0114293 A1 | 5/2009 | Kanai et al. | |
| 2010/0092767 A1 * | 4/2010 | Naito | B29C 59/14 |
| | | | 428/336 |
| 2010/0151231 A1 | 6/2010 | Matsuo et al. | |
| 2014/0332674 A1 * | 11/2014 | Goto | G01N 30/74 |
| | | | 250/227.11 |

FOREIGN PATENT DOCUMENTS

| | | |
|---|---|---|
| JP | 4337935 B2 | 9/2009 |
| JP | 2011-245675 A | 12/2011 |
| WO | 2007049332 A1 | 5/2007 |
| WO | 2008/105068 A1 | 9/2008 |
| WO | WO2013084626 A * | 6/2013 |

* cited by examiner

GLASS/RESIN COMPOSITE STRUCTURE AND METHOD FOR MANUFACTURING SAME

TECHNICAL FIELD

The present invention relates to a composite structure of a glass substrate bonded to a resin substrate that is suitable for a flow channel and a method for producing the same.

BACKGROUND ART

Use of a wide variety of solvents is required for general-purpose liquid analyzers represented by flow injection analyzers and liquid chromatography apparatuses, and, in general, flow channels in such apparatuses are required to have excellent chemical resistance and high pressure resistance. As materials that satisfy such requirements, organic materials, such as super engineering plastics including polyether ether ketone resin (hereafter abbreviated as "super enpla"), and inorganic materials, such as silica glass and stainless steel, are known. In particular, a combination of silica glass with polyether ether ketone resin is suitable for a material constituting a flow cell for photometric analysis because of properties of silica glass, such as high light permeability in an extensive wavelength region, excellent chemical resistance, and high stress tolerance, and properties of super enpla, such as excellent moldability and processability, excellent chemical resistance, and high stress tolerance. Accordingly, various bonding techniques have heretofore been attempted. The simplest method for bonding silica glass to resin comprises dissolving resin in a solvent, bringing liquefied resin into close contact with silica glass, and removing the solvent by evaporation. In the case of a material such as super enpla with excellent chemical resistance, however, there has been no sufficient solubilizing solvent, and the method as described above could not be employed.

Accordingly, a method of bonding involving the use of an adhesive agent and a method of bonding via pressure bonding had been employed. When polyether ether ketone resin is bonded to silica glass via the former method, for example, a method of bonding involving the use of an adhesive agent, such as epoxy-based resin or acrylic resin, is recommended. In the case of the latter method, a method making use of a configurational change caused by volume expansion or contraction, such as shrinkage fit or cooling fit, and a method of using a configurational change caused by plastic deformation involving the use of ferrules and nuts have been developed. As another method associated with plastic deformation, a method of bonding comprising heating resin to its melting point or higher, bringing the liquefied resin into close contact with silica glass, and cooling the resultant to resolidify it is known.

As an attempt to allow silica glass to chemically bind to resin, a method of bonding comprising forming membranes containing siloxane groups on both silica glass and resin substrate surfaces via plasma polymerization, and heating the substrates at a low temperature of 100° C. or lower so as to fix the membranes formed via plasma polymerization to each other via polymerization of siloxane groups has been reported (Patent Document 1).

PRIOR ART DOCUMENTS

Patent Documents

Patent Document 1: JP 4,337,935 B2

SUMMARY OF THE INVENTION

Objects to be Attained by the Invention

According to a conventional technique, it was impossible to produce a composite structure with high pressure resistance that would be suitable for a flow channel by reducing the number of components while maintaining the excellent chemical resistance and high chemical resistance inherent in silica glass and super enpla.

According to a method involving the use of an adhesive agent, in the case of polyether ether ketone resin, for example, epoxy resin or acrylic resin at the bonded interface has low resistance to organic solvents and acid-base solvents. This disadvantageously causes the chemical resistance of the entire composite structure to deteriorate, and chemical resistance of silica glass and polyether ether ketone resin cannot be utilized.

According to a method employing pressure bonding, silica glass components are damaged when high degrees of stress are applied. Thus, high stress cannot be applied, and pressure resistance disadvantageously remains as low as about several MPa. In addition, a method employing pressure bonding requires the use of an increased number of components in order to support the contact plane between the silica glass component and the super enpla component. According to a method comprising heat-melting super enpla so as to fuse the same to deposit it onto silica glass, further, affinity at the interface between silica glass and super enpla is low, and silica glass and super enpla repel each other. When super enpla is peeled from the glass as it shrinks at the time of resolidification during the cooling process, gaps are formed at the interface, and liquid leaks through such gaps.

In general, the surface tension between silica glass and super enpla is high. When both silica glass and super enpla are flat plates, accordingly, a configuration of super enpla is altered so as to minimize the energy, and silica glass is brought into point-contact with super enpla, as shown in FIG. 24. The influence of lowered pressure resistance caused thereby becomes significant when silica glass and super enpla are cylindrical tubes, as shown in FIG. 25. When a substance having affinity higher than that of silica glass, such as resin of the same type or stainless steel, is provided around super enpla, in particular, super enpla shrinks toward the substance with higher affinity during the process of cooling. Thus, super enpla would be peeled from the silica glass surface at an accelerated speed. While FIG. 25 shows an embodiment in which the outer cylindrical tube is made of super enpla and the inner cylindrical tube is made of silica glass, the same phenomena would naturally occur if the material constituting the outer cylindrical tube were to be replaced with the material constituting the inner cylindrical tube. In order to avoid such phenomena, it is necessary to apply stress to the contact plane between super enpla and silica glass when super enpla is to be resolidified. However, this method involves pressure bonding and, accordingly, the problem described above remains unresolved.

According to a method of allowing silica glass to chemically bind to resin by heating both materials at a low temperature of 100° C. or lower, as shown in FIG. 26, the substrates are brought into point-contact with each other due to irregularities on the substrate surface, gaps are formed at the interface, and pressure resistance is lowered as a consequence. When a substrate is in a tubular form such as a cylindrical tube, as shown in FIG. 27, the substrates are brought into point-contact with each other because of gaps resulting from dimensional tolerance caused at the time of processing, gaps are formed at the interface, and pressure resistance is lowered as a consequence, disadvantageously. As with the case shown in FIG. 25, the same problem would arise even if materials constituting the substrates were to be replaced with each other.

Under the above circumstances, the present invention is intended to provide a composite structure with high pressure resistance that is suitable for a flow channel while maintaining high chemical resistance inherent in silica glass and super enpla and a method for producing the same.

Means for Attaining the Objects

A method for producing the composite structure provided with a flow channel and constituted of a glass substrate and a resin substrate according to the present invention comprises: a step of modifying a glass substrate surface with a hydrolyzable silicon compound; a step of bringing the glass substrate into contact with the resin substrate; and a step of heating the contact plane between the glass substrate and the resin substrate to a temperature from the glass transition temperature to the pyrolysis temperature of the resin substrate, eliminating gaps between the glass substrate and the resin substrate to bring them into close contact with each other, and causing chemical bonding and/or anchor effects between the glass substrate and the resin substrate via the hydrolyzable silicon compound. According to a representative embodiment, the glass substrate is a silica glass substrate, and the resin substrate is a super enpla substrate.

Preferably, the method of modification with a hydrolyzable silicon compound is wet coating involving the use of a solution of a hydrolyzable silicon compound, and the hydrolyzable silicon compound is a silicon compound having an alkoxy group. Also, it is preferable that the contact plane between the silica glass substrate and the super enpla substrate be heated to a temperature from the melting point to the pyrolysis temperature of the super enpla. The flow channel may be provided inside the silica glass substrate or the super enpla substrate in advance, or a flow channel may be formed when these substrates are bonded to each other.

The composite structure of the present invention is composed of the glass substrate bonded to the resin substrate in which a flow channel is provided. On the contact plane between the glass substrate and the resin substrate, the angle of the end planes of the region at which the resin substrate is bonded to the interface is 0 degrees to 90 degrees.

Effects of the Invention

By heating the contact plane between the silica glass substrate and the super enpla substrate to the glass transition temperature or higher of the super enpla, super enpla is softened or liquefied, gaps between the silica glass and the super enpla are eliminated, the silica glass substrate is brought into surface-to-surface contact with the super enpla substrate, and adhesion therebetween is improved as a consequence. In addition, chemical bonding takes place via a hydrolyzable silicon compound between the silica glass and the super enpla at a high temperature of the glass transition temperature or higher, and affinity between the silica glass and the super enpla is improved as a consequence. Further, anchor effects arise as the softened or liquefied super enpla enters into the hydrolyzable silicon compound, and friction between the silica glass and the super enpla is improved. Thus, the composite structure can achieve high-pressure resistance. As the secondary effects, super enpla forms a convex configuration against silica glass on the end plane of the region in which silica glass adheres to super enpla, the effective area of adhesion is increased, and stress concentration is thereby relieved. Thus, pressure resistance is improved. According to the process of the present invention, such effects can be achieved in a single step, and the number of components and the number of steps can be minimized.

Objectives, constitutions, and effects other than those described above are demonstrated in the embodiments described below.

EMBODIMENTS FOR CARRYING OUT THE INVENTION

Figure 1:
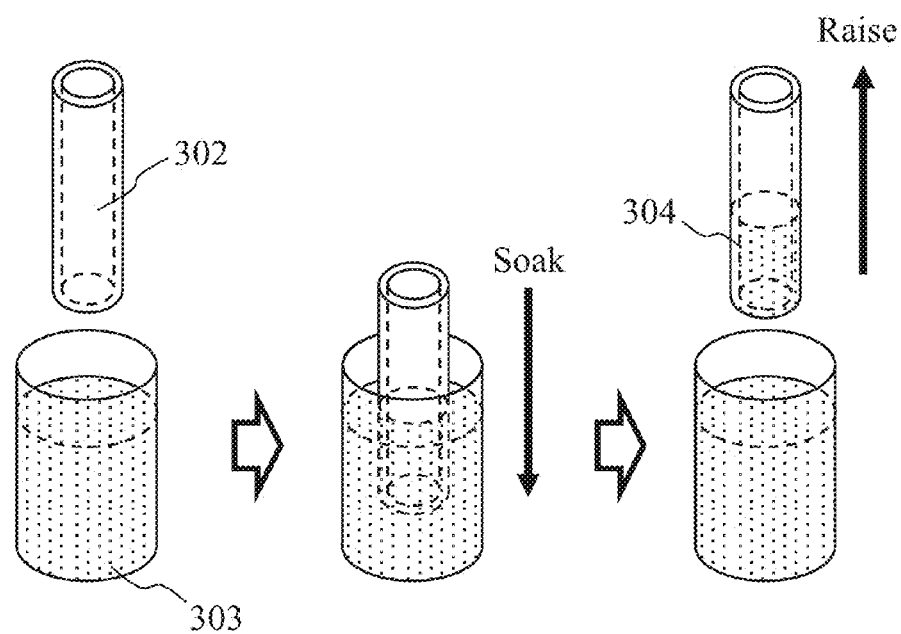
FIG. 1 shows a process for producing a composite structure provided with a flow channel according to an embodiment of the present invention.

Hereafter, embodiments of the present invention are described with reference to the drawings.

In the method of production according to the present invention, a silica glass substrate may be a compound mainly composed of silicon that can chemically bind to a hydrolyzable silicon compound. Preferable examples include synthetic silica glass, fused-silica glass, borosilicate glass, and soda glass having excellent light permeability. According to the present invention, a super enpla substrate is composed of a material having low affinity with silica glass in a softened or liquefied state; that is, a material exhibiting high surface tension between the silica glass and the super enpla. Polyallyl ether ketone-based resins, and, typically, polyether ether ketone resin, polyether ketone resin, polyether ketone ketone resin, polyether nitrile resin, and other resins are preferable. Polysulfone-based resins, such as polysulfone resin, polyphenylene sulfide resin, polyether sulfone resin, and polyphenylsulfone resin, polyimide resins, or polyamide-based resins may be, for example, polyimide-based resin, polyetherimide resin, polyamide resin, or polyamide imide resin. While the engineering plastics described above are preferable in order to sufficiently achieve the effects of the present invention, other general-purpose plastics, such as polycarbonate resin, acrylic resin, epoxy resin, or fluorine-based resin, such as polytetrafluoroethylene resin or polytetrafluoroethylene-polyhexafluoropropylene resin, may be used.

In the method of production according to the present invention, the silica glass substrate surface is first modified with a hydrolyzable silicon compound. A hydrolyzable silicon compound may be a silicon compound comprising an alkoxy group, and an alkoxy group preferably has an alkyl group, such as a methoxy, ethoxy, propoxy, or butoxy group. A hydrolyzable silicon compound may be a monomer, such as tetraethoxysilane, or a polymer thereof, such as a polytetraethoxysilane compound. A polymer is less likely to undergo self-polymerization, it is more stable, and it is easier to handle, in comparison with a monomer. Thus, a polymer is preferable. A preferable solvent for a hydrolyzable silicon compound is less likely to undergo self-polymerization, and an alkyl alcohol having a number of carbon atoms that is the same as or close to that of an alkyl group in the alkoxy group is desirable. In the case of a polytetraethoxysilane compound, for example, a solvent is preferably ethanol, propyl alcohol, isopropyl alcohol, or butanol.

The silica glass substrate surface may be coated with a solution containing a hydrolyzable silicon compound by a general wet coating technique. Examples of preferable techniques include dip coating, spin coating, and spray coating, so that membrane thickness can be regulated. Post-coating treatment is preferably a technique that modifies the substrate surface while maintaining hydrolyzability to a considerable extent, as described below. In the case of a polytetraethoxysilane compound that is a polymer, for example, dehydration may be carried out at room temperature. In contrast, it is necessary that a monomer (i.e., tetraethoxysilane) be subjected to pre-treatment at high temperature (100° C. to 200° C.) after coating, in order to form a membrane of a certain thickness. Thus, a hydrolyzable silicon compound is chemically bound to and made to tightly adhere to the silica glass substrate surface. In addition to wet coating, the CVD or PVD method may be employed.

The silica glass substrate modified with the hydrolyzable silicon compound in the manner described above is brought into contact with the super enpla substrate, and the contact plane between the silica glass substrate and the super enpla substrate is heated to the glass transition temperature or higher of the super enpla substrate. The heating temperature may be the glass transition temperature or higher at which the super enpla substrate is softened and adheres more tightly to the silica glass substrate to the pyrolysis temperature. The heating temperature is preferably in a range from the melting point at which the super enpla substrate is liquefied to the pyrolysis temperature. By heating the super enpla substrate to its glass transition temperature or higher, softened or liquefied resin enters into irregular gaps at the interface between the substrates, and the contact between the substrates is improved from point contact to surface-to-surface contact. In such case, the hydrolyzable silicon compound modifying the silica glass surface is hydrolyzed by thermal energy at a temperature higher than the glass transition temperature, and it is chemically bound to the super enpla substrate. Thus, affinity between these substrates is significantly improved, and the substrates are tightly adhered to each other.

The hydrolyzable silicon compound forms a structure having micro-gaps of several angstroms (Å) to several nanometers (nm) on the silica glass surface. Thus, the softened or liquefied super enpla substrate enters into the gaps, anchor effects are exerted and friction is enhanced to a significant extent, and the substrates adhere more tightly to each other. The term "anchor effects" used herein refers to effects resulting when mechanical strength is enhanced as a result of softened or liquefied resin entering into micro-gaps on the substrate surface and hardening.

Heating may be carried out by heating the entire structure with the use of, for example, an incubator or electric furnace. When a part of the structure is to be topically heated, for example, heat is transferred from the silica glass substrate side using a hot plate heated while applying an electric current, so as to heat the contact plane between the silica glass substrate and the super enpla substrate. Alternatively, a heating wire capable of heating to a high temperature with the application of an electric current may be provided in the vicinity of the contact plane between the silica glass substrate and the super enpla substrate in advance and heat may be applied later. Further, a heat-transfer member capable of heating via electromagnetic induction, such as stainless steel, may be provided in the vicinity of the contact plane between the silica glass substrate and the super enpla substrate, and heat may be applied with the aid of the heat-transfer member by so-called induction heating by which a high-frequency magnetic field of several tens to several hundreds of kHz is applied. In addition, the adhesion plane may be selectively heated by ultrasonic waves, for example. Alternatively, induction heating using a high frequency of several tens to several hundreds of MHz that allow the super enpla substrate to produce heat may be carried out. Heating may be carried out by supplying a certain quantity of heat or instantaneously supplying a thermal pulse. When the heating temperature is from the glass transition temperature to the melting point (from the glass transition temperature to the pyrolysis temperature in case of a material for which there is no melting point), it is preferable that stress be applied to a region between the silica glass substrate and the super enpla simultaneously with heating, in order to improve the adhesion strength. Super enpla may be cooled naturally or forcibly when it is to be resolidified.

In the following examples, the composite structure composed of a silica glass substrate and a super enpla substrate and provided with a flow channel according to the present invention and the method for producing the same are described. In the following examples, a representative super enpla; i.e., polyether ether ketone resin, was used.

Figure 2:
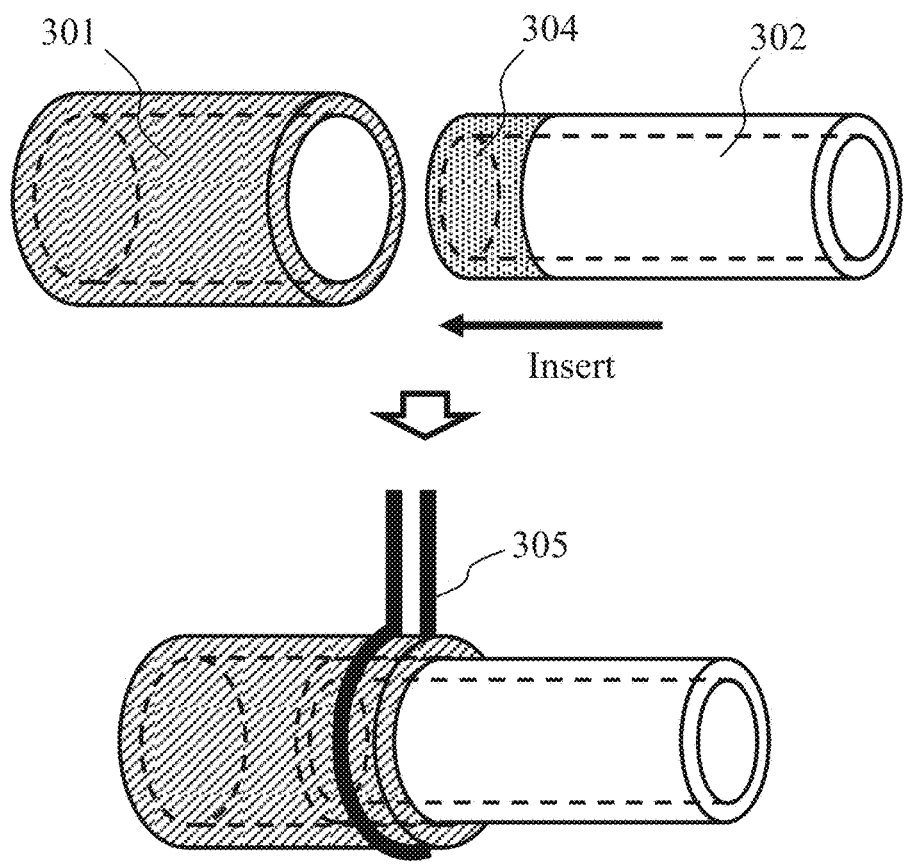
FIG. 2 shows a process for producing a composite structure provided with a flow channel according to an embodiment of the present invention.

FIG. 1 and FIG. 2 each show a composite tubing provided with a flow channel according to an embodiment of the present invention. A composite tubing is constituted by a first cylindrical tube 301 made of polyether ether ketone resin and a second cylindrical tube 302 made of silica glass having an outer diameter that is less than the inner diameter of the first cylindrical tube. With the use of a solution 303 containing a hydrolyzable silicon compound, as shown in FIG. 1, the second cylindrical tube 302 was modified with a hydrolyzable silicon compound 304 via dip coating by soaking the second cylindrical tube 302 in the solution and raising the same from the solution. As shown in FIG. 2, the second cylindrical tube 302 was then inserted into the first cylindrical tube 301, and the resultant was heated to a temperature from the glass transition temperature (143° C.) to the pyrolysis temperature (450° C.) of the polyether ether ketone resin using a heating wire 305 in a form capable of covering the contact plane between the first cylindrical tube and the second cylindrical tube (e.g., a circular or C-shaped form), so as to produce a composite tubing in which the surfaces to be bonded were tightly adhered to each other. In such a case, the heating temperature is preferably adjusted between the melting point (343° C.) and the pyrolysis temperature (450° C.) of polyether ether ketone resin to enhance the fluidity, thereby increasing the area of surface-to-surface contact between the substrates.

Figure 3:
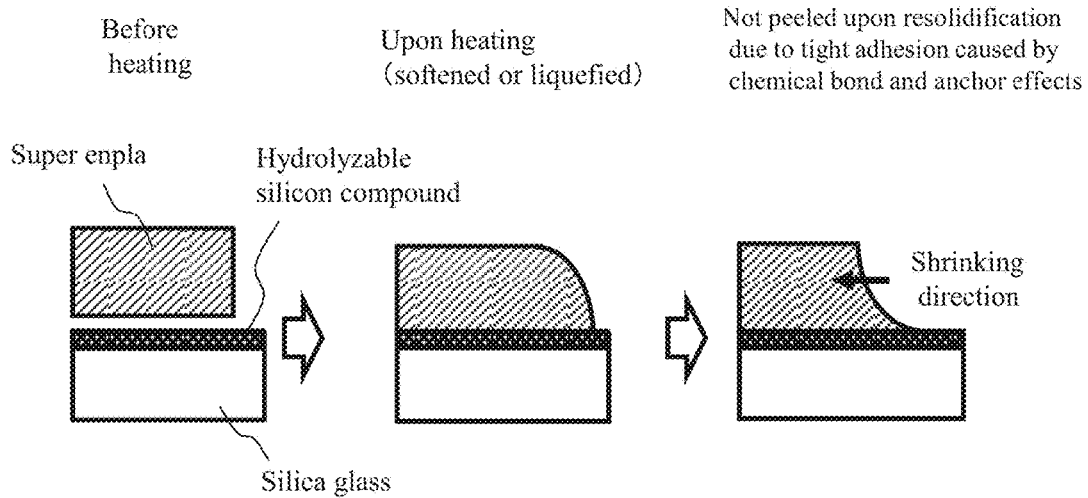
FIG. 3 schematically illustrates the behavior of the adhesion plane between silica glass and super enpla in the steps of heating and cooling according to the present invention.
Figure 4:
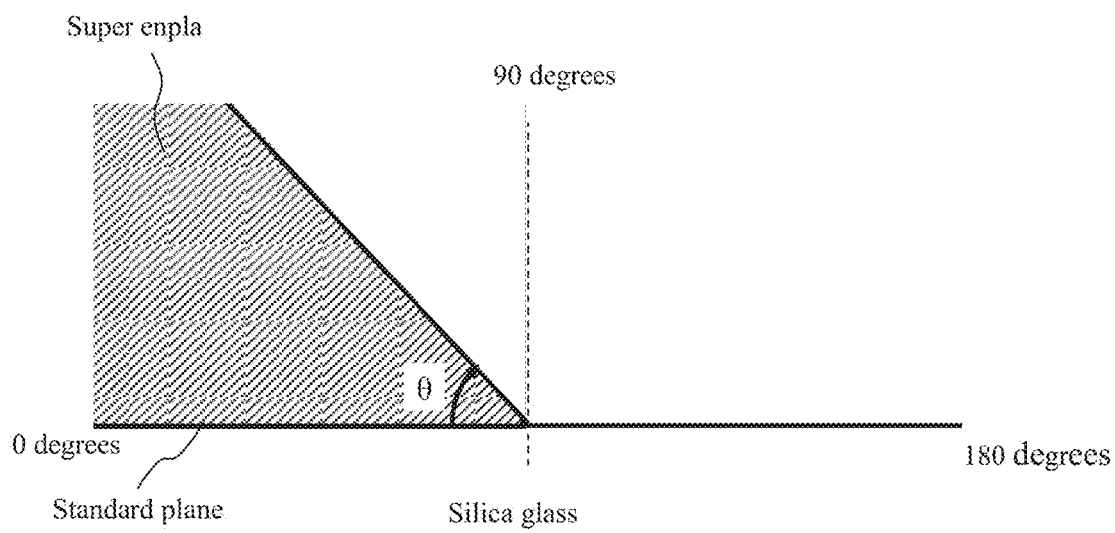
FIG. 4 illustrates the angle of the end plane of a region in which super enpla is bonded to silica glass with respect to the adhesion plane according to the present invention.

As shown in FIG. 3, polyether ether ketone resin that is heated to a temperature equivalent to or higher than its melting point is softened or liquefied and then it adheres to the silica glass. Such polyether ether ketone resin adheres tightly to the silica glass via chemical bonding and anchor effects when it is resolidified. Thus, peeling that occurs according to a conventional technique can be prevented. In this process, polyether ether ketone resin tends to shrink toward its center, and the adhesion plane between the polyether ether ketone resin and the silica glass is tightly bonded. Accordingly, the polyether ether ketone resin shrinks in a manner such that it is dragged to the adhesion plane between the resin and the silica glass. As a result, as shown in FIG. 3, the end plane of a region in which the polyether ether ketone resin is bonded to the silica glass forms a configuration such that the polyether ether ketone resin wets the silica glass. More specifically, as shown in FIG. 4, the contact plane between silica glass and polyether ether ketone resin is designated as the standard plane, and the angle (θ) formed by the end plane of a region in which the polyether ether ketone resin is bonded to the silica glass with respect to the standard plane is from 0 degrees to 90 degrees (hereafter referred to as "convex configuration" for the convenience of explanation).

Figure 5:
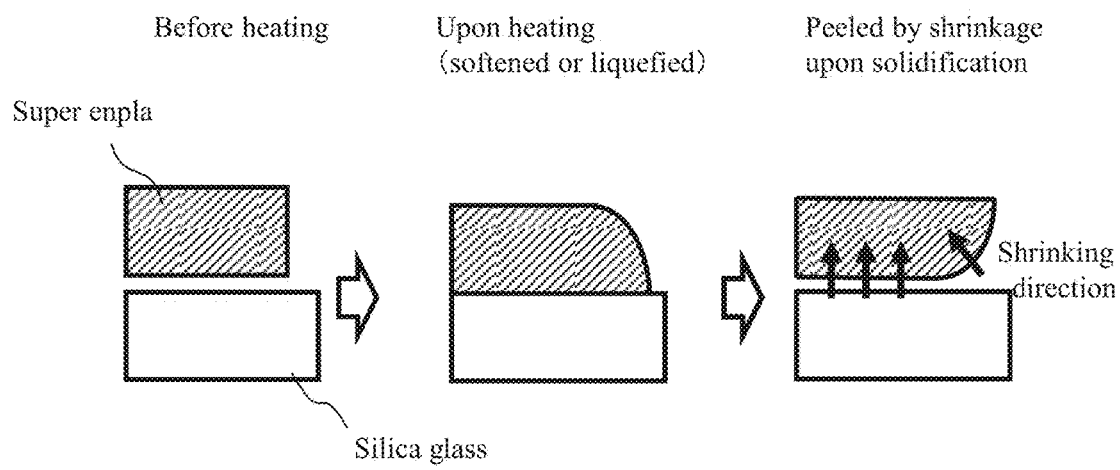
FIG. 5 schematically illustrates the behavior of the adhesion plane between silica glass and super enpla in the steps of heating and cooling according to a conventional technique.
Figure 6:
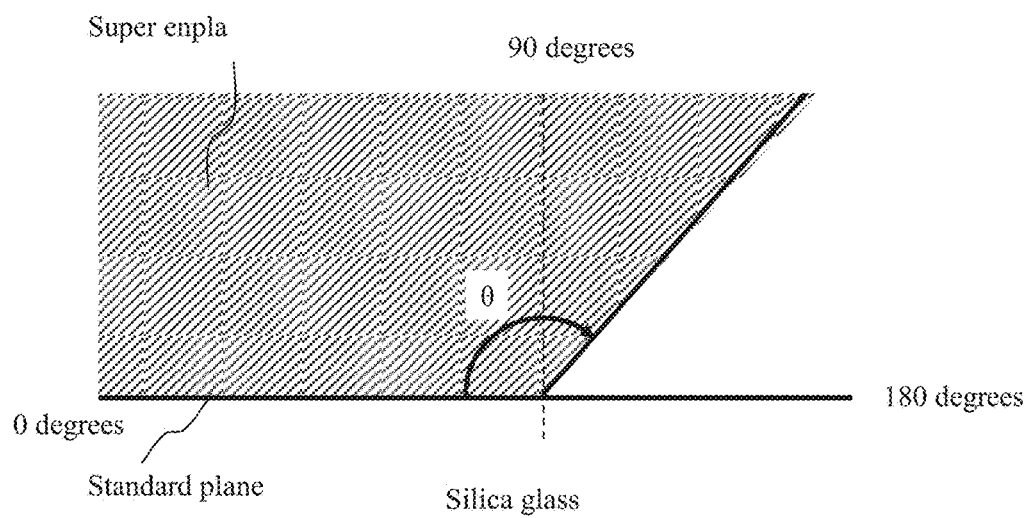
FIG. 6 illustrates the angle of the end plane of a region in which super enpla is bonded to silica glass with respect to the adhesion plane according to a conventional technique.

According to a conventional technique, however, a configuration such that the polyether ether ketone resin repels the silica glass is formed because of low affinity between the polyether ether ketone resin and the silica glass, as shown in FIG. 5. More specifically, as shown in FIG. 6, the contact plane between silica glass and polyether ether ketone resin is designated as the standard plane, and the angle (θ) formed by the end plane of a region in which the polyether ether ketone resin is bonded to the silica glass with respect to the standard plane is from above 90 degrees to 180 degrees (hereafter referred to as a "concave configuration" for the convenience of explanation). In such a concave configuration, the effective area of adhesion between the polyether ether ketone resin and the silica glass is decreased. In addition, stress is often concentrated at a single minute point in such a concave configuration, which leads to breakage of components and then causes leakage of liquid. In the case of a convex configuration according to the present invention, however, the effective area of adhesion between the polyether ether ketone resin and the silica glass is increased, and stress is not concentrated at a particular single point, unlike the concave configuration. Thus, pressure resistance is improved.

Figure 7:
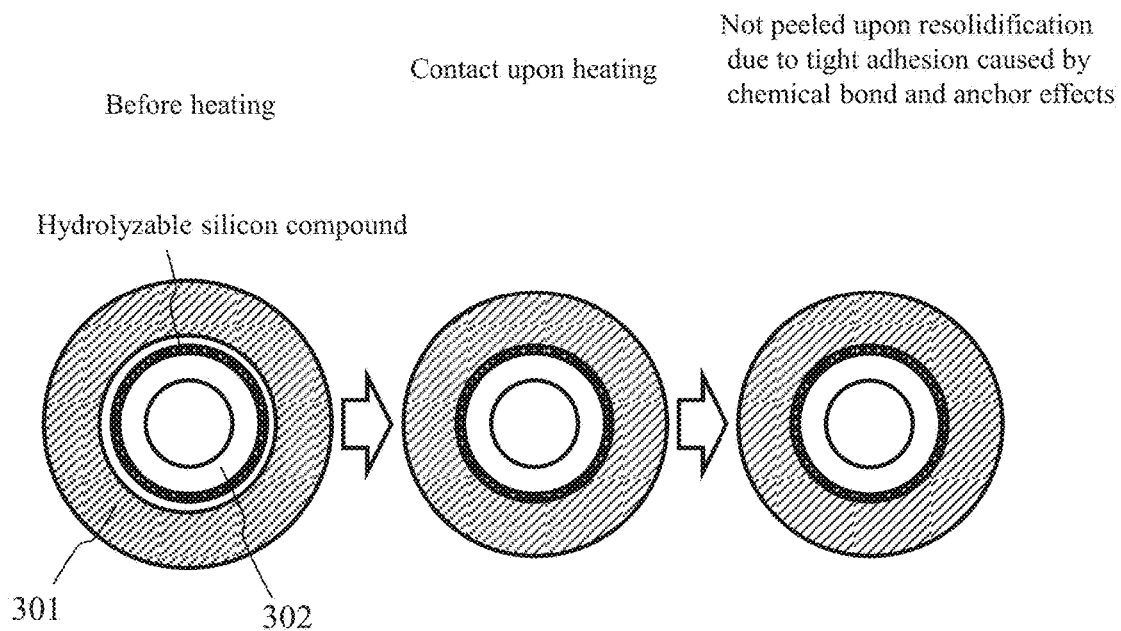
FIG. 7 schematically illustrates the behavior of a cross section of the adhesion plane of silica glass and super enpla in the steps of heating and cooling according to the present invention.

Accordingly, the first cylindrical tube 301 is tightly adhered to the second cylindrical tube 302 as shown in FIG. 7, no gap is formed at the interface, and a composite tubing with pressure resistance higher than that achieved via pressure bonding can be achieved. The initial gap between the first cylindrical tube and the second cylindrical tube is preferably as minute as possible prior to adhesion. From the viewpoint of engagement of components and retention of a super enpla substrate configuration upon heating, the initial gap is preferably 1 μm to 500 μm. According to a dip coating method, areas other than the contact plane between the first cylindrical tube and the second cylindrical tube remain coated with hydrolyzable silicon compounds. By baking the composite structure (e.g., at 120° C. for 20 minutes) following preparation thereof, a remaining unreacted hydrolyzable silicon compound can be inactivated. Since the inactivated hydrolyzable silicon compound has a chemical structure very similar to that of the silica glass substrate, properties of the silica glass substrate would not be damaged. It is deduced that the reaction between the polyether ether ketone resin and the hydrolyzable silicon compound take place between an ether, carbonyl, or phenyl group in the polyether ether ketone resin and an alkoxy group in the hydrolyzable silicon compound cleaved via hydrolysis.

In the case of super enpla other than polyether ether ketone resin, the glass transition temperature of, for example, polyphenylene sulfide resin is 85° C., the melting point thereof is 285° C., and the pyrolysis temperature thereof is 480° C. Also, the glass transition temperature of a polyamide resin PA66 is 50° C., the melting point thereof is 265° C., and the pyrolysis temperature thereof is 454° C. Accordingly, it is necessary that the heating temperature be adequately adjusted, so that temperatures thereof remain within the ranges described above.

This embodiment is useful when connecting a device that is connected to a polyether ether ketone resin tubing to another device that is connected to a silica glass tubing. For example, this embodiment can be applied when connecting a polyether ether ketone resin tubing to a flow cell composed of silica glass. It can also be applied to connect both ends of a glass capillary of a liquid chromatography apparatus or to connect both ends of a glass capillary of a gas chromatography apparatus.

The structure provided with a flow channel according to the present invention is preferably used as a flow cell for a liquid analyzer. Specifically, it is also preferably used as a flow cell for photometric analysis in a flow injection analyzer or a liquid chromatography apparatus. A flow cell for a liquid analyzer is required to have high pressure resistance. Accordingly, a mechanical fastening mechanism using a screw or the like was necessary in the past, and the number of components was very large. According to the present invention, the number of components constituting a flow cell can be reduced, and pressure resistance superior to that attained by a conventional technique can be achieved because of the plurality of pressure-resistance-improving effects described above.

Figure 8:
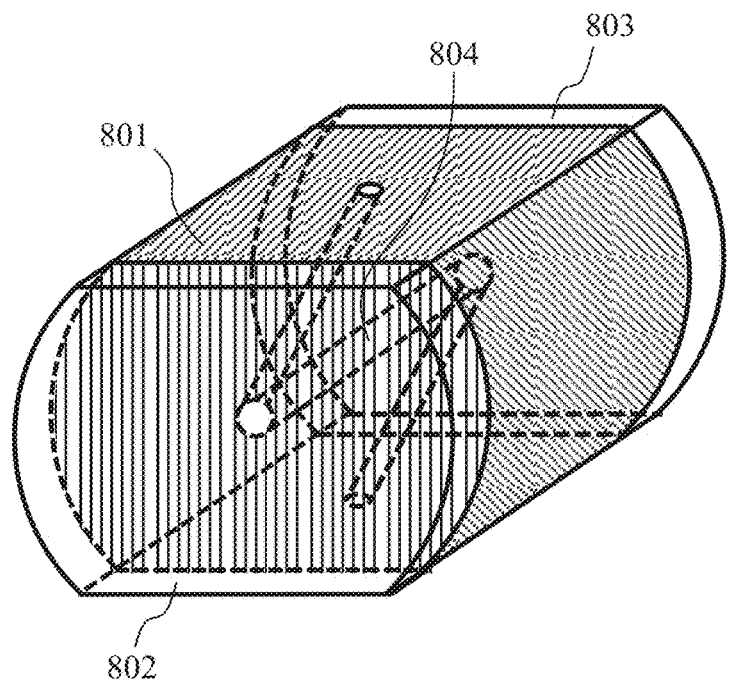
FIG. 8 shows a perspective view of the composite structure provided with a flow channel according to an embodiment of the present invention.
Figure 9:
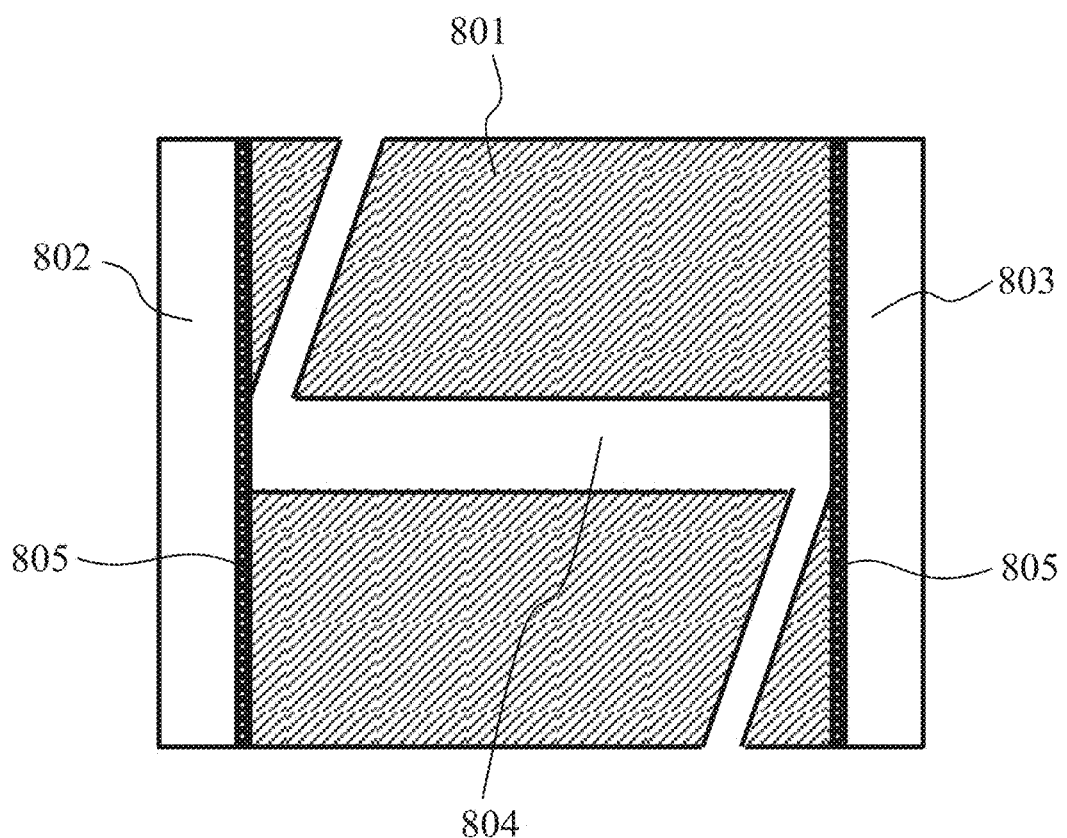
FIG. 9 shows a cross-sectional view of the composite structure provided with a flow channel according to an embodiment of the present invention.
Figure 10:
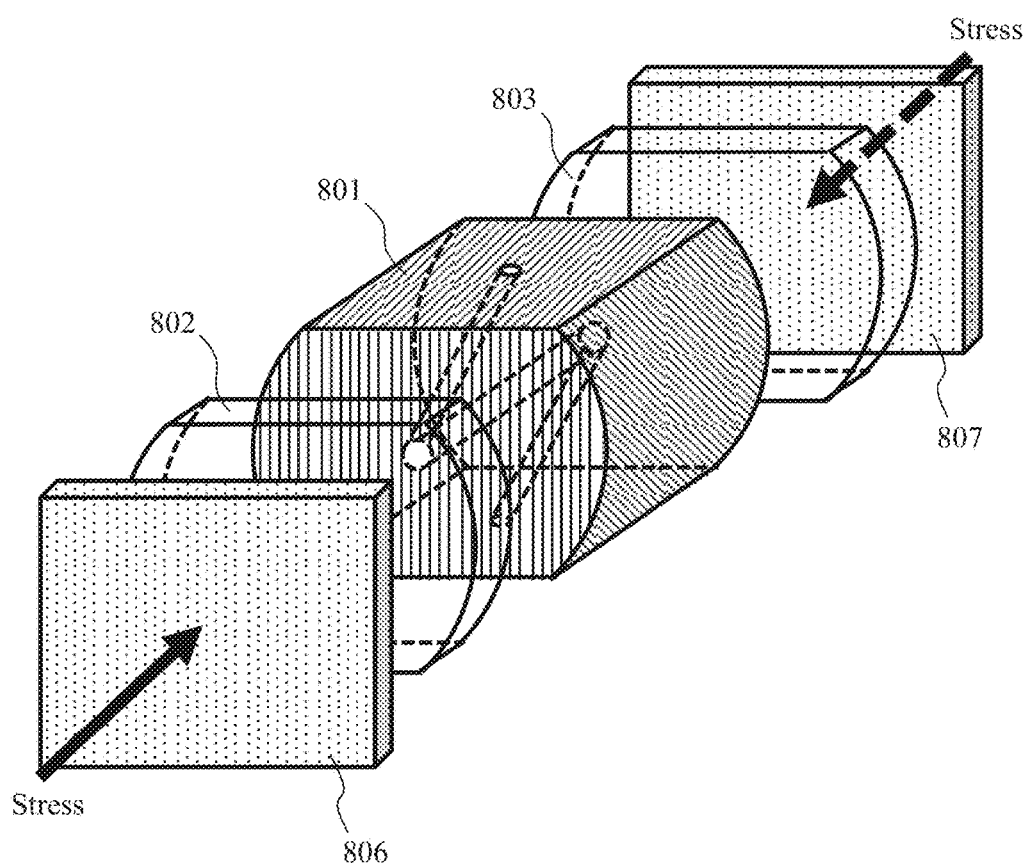
FIG. 10 shows an illustrative view showing a process for producing the composite structure provided with a flow channel according to an embodiment of the present invention.

FIG. 8 and FIG. 9 each show a flow cell for a liquid analyzer according to an embodiment. FIG. 8 and FIG. 9 show a perspective view and a cross-sectional view of the same flow cell. This flow cell is composed of a cell body 801 made of polyether ether ketone resin and window materials 802 and 803 made of silica glass. A flow channel 804 is provided in advance inside the cell body 801. In the flow channel 804, in particular, a region of the flow channel opened in a direction perpendicular to the window materials 802 and 803 serves as an optical path through which light is transmitted. The window materials 802 and 803 are modified with a hydrolyzable silicon compound 805 via dip coating. Thereafter, as shown in FIG. 10, the cell body 801 is subjected to thermal pressure bonding with the window materials 802 and 803 by sandwiching the same with heating plates 806 and 807 that had been heated to a temperature equivalent to or higher than the melting point of the polyether ether ketone resin via electric current heating. In such a case, the heating temperature is adjusted to a temperature equivalent to or higher than the melting point of the polyether ether ketone resin, so that the window materials 802 and 803 are tightly adhered to the cell body 801, and a flow cell with high pressure resistance can be produced. In order to prevent the polyether ether ketone resin from becoming deformed and the configuration of the flow channel from being different from the initial configuration, also, it is preferable that heating be carried out with the application of thermal pulses and that bonding be completed in as short a time period as possible. FIG. 8 shows a cylindrical optical path. In order to suppress the spatial spreading of the sample, the inner diameter of the cross section thereof is preferably 0.05 mm to 2 mm. The length of the optical path in the cell body is preferably 0.1 mm to 20 mm. While a cell body provided with a representative cylindrical optical path is inspected as a flow cell for a liquid analyzer in FIG. 8, an optical path may be in the form of, for example, an ellipse tubing, polygonal tubing, or tapered cylindrical tubing.

Figure 11:
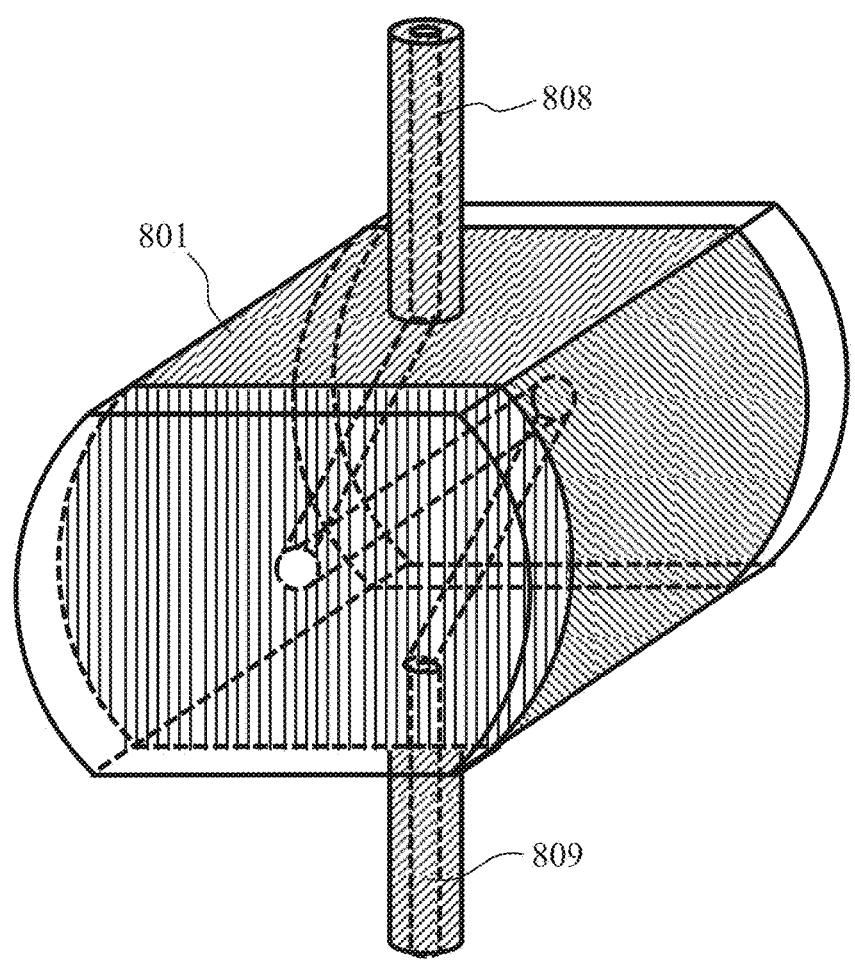
FIG. 11 shows a perspective view of the composite structure provided with a flow channel according to an embodiment of the present invention.

As shown in FIG. 11, tubings 808 and 809 made of polyether ether ketone resin may be bonded to the inlet and the outlet of the flow channel 804 in the cell body 801 provided with the window materials as shown in FIG. 8 in the manner described below. Areas in the vicinities of the contact planes between the cell body and the tubings 808 and 809 are each heated to a temperature equivalent to or higher than the melting point of the polyether ether ketone resin using heating wires in a form capable of covering the tubings 808 and 809. The contact planes are allowed to liquefy and then naturally cooled to resolidify. Thus, the cell body is integrated with the tubings 808 and 809. In order to facilitate bonding, it is preferable that the forms of the inlet and the outlet of the flow channel 804 in the cell body 801 be modified in advance so as to fit with the outer diameter of the tubing. In order to prevent the tubings from clogging upon heating, commercially available tubings each composed of a polyimide-coated glass cylinder coated with polyether ether ketone resin are preferably used as the tubings 808 and 809. As described above, a flow cell with the minimized number of components and high pressure resistance can be produced.

Figure 12:
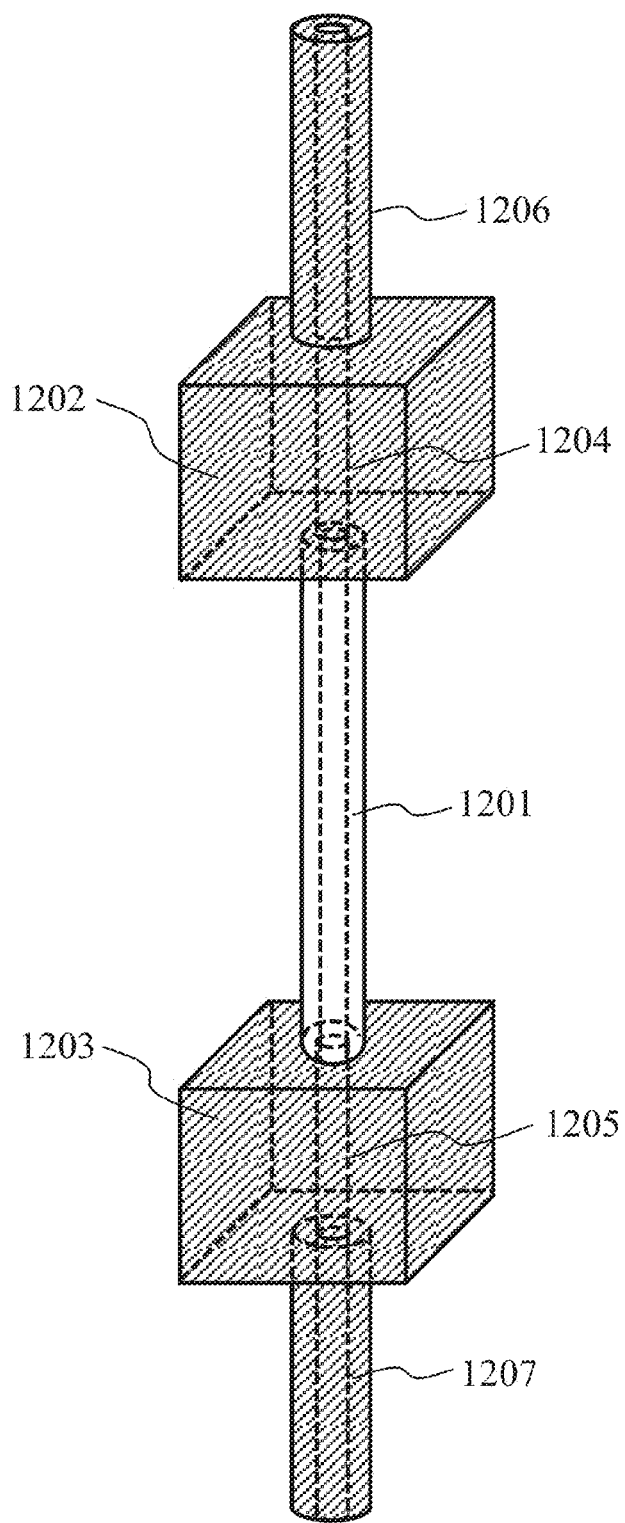
FIG. 12 shows a perspective view of the composite structure provided with a flow channel according to an embodiment of the present invention.
Figure 13:
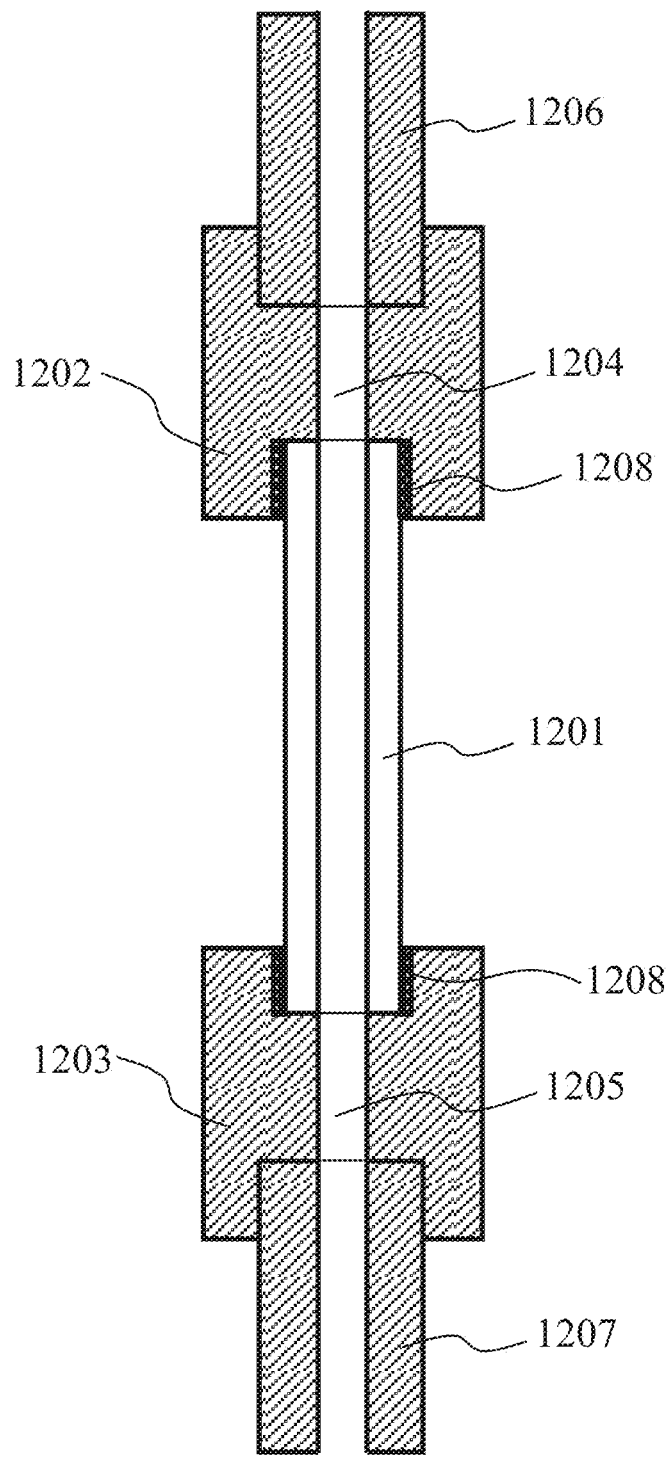
FIG. 13 shows a cross-sectional view of the composite structure provided with a flow channel according to an embodiment of the present invention.

FIG. 12 and FIG. 13 each show a flow cell for a liquid analyzer according to another embodiment. FIG. 12 and FIG. 13 show a perspective view and a cross-sectional view of the same flow cell. This flow cell is composed of a cylindrical cell body 1201 made of silica glass, two-way joints 1202 and 1203 comprising flow channels 1204 and 1205 and made of polyether ether ketone resin, and tubings 1206 and 1207 made of polyether ether ketone resin. The cell body 1201 is modified with a hydrolyzable silicon compound 1208 via dip coating, and the two-way joints 1202 and 1203 are brought into contact with the two-way joints 1202 and 1203. With the use of a heating wire in a shape capable of covering the interface between the two-way joints 1202 and 1203 and the cell body 1201, the structure is heated from the cell body 1201 side to a temperature equivalent to or higher than the melting point of the polyether ether ketone resin. Thus, the cell body 1201 is tightly adhered to the two-way joints 1202 and 1203. The tubings 1206 and 1207 are heated to a temperature equivalent to or higher than the melting point of the polyether ether ketone resin using a heating wire while they are kept in contact with the two-way joints 1202 and 1203, and a flow cell comprising the cell body 1201, the two-way joints 1202 and 1203, and the tubings 1206 and 1207 tightly adhered to each other can be produced.

This flow cell structure is used for analysis in a space with a micro volume in a liquid analyzer. Specifically, it is used for analysis having priority in a reduction of a space in which the sample spreads over sensitivity. Examples of detection methods include a method in which light is allowed to permeate vertically with respect to the direction of liquid flow in a cylindrical tube and the absorbance is measured and a method in which excited light is applied and fluorescence is received. For example, an inner diameter of a cylindrical tube is preferably 1 μm to 1 mm so as to minimize the space in which the sample spreads. A cylindrical tube length is preferably 0.1 mm to 1 mm.

Figure 14:
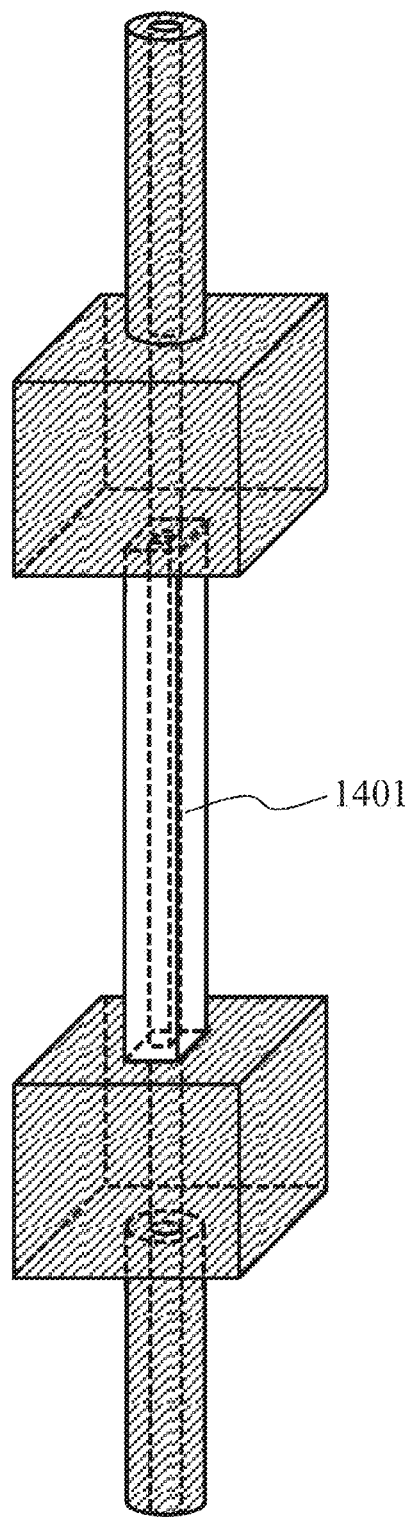
FIG. 14 shows a perspective view of the composite structure provided with a flow channel according to an embodiment of the present invention.

While a cylindrical tube is exemplified as a form of a cell body in FIG. 12, a cell body may be a polygonal tube. When fluorescence analysis is performed, in particular, it is necessary that the amount of light excited and fluorescence scattered be reduced. As shown in FIG. 14, accordingly, a cell body 1401 is preferably composed of a rectangular tube, so that the amount of light scattered is small.

Figure 15:
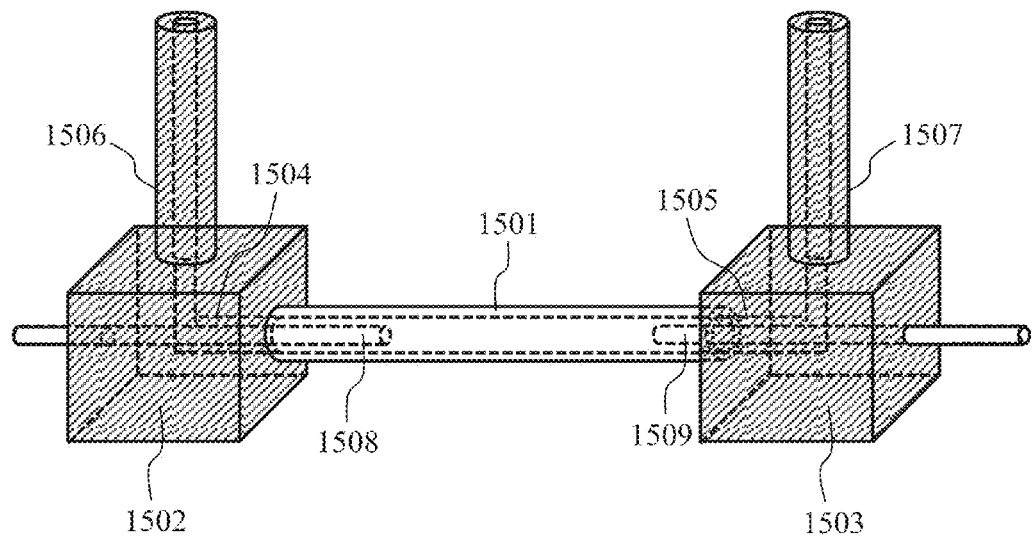
FIG. 15 shows a perspective view of the composite structure provided with a flow channel according to an embodiment of the present invention.
Figure 16:
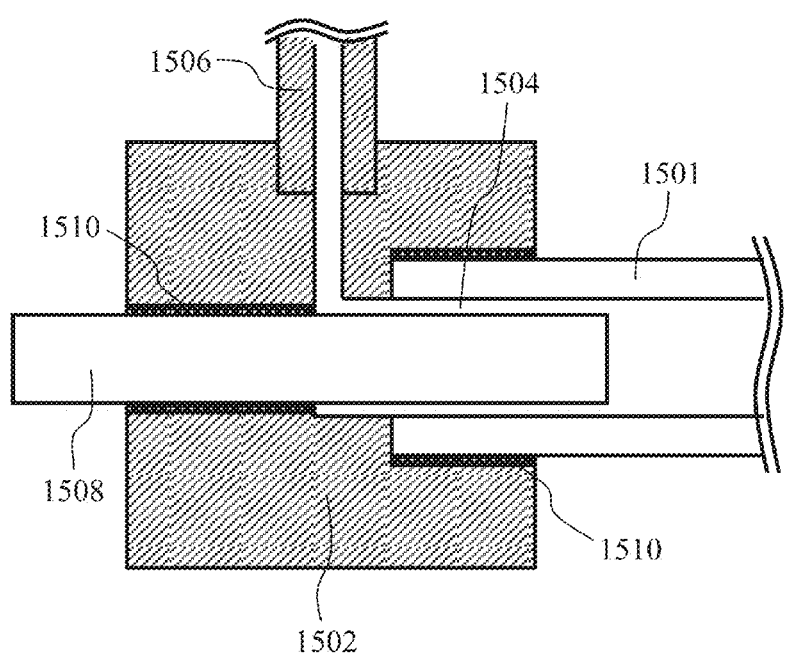
FIG. 16 shows a cross-sectional view of the composite structure provided with a flow channel according to an embodiment of the present invention.

FIG. 15 and FIG. 16 each show a flow cell for a liquid analyzer according to another embodiment. FIG. 15 shows a perspective view of a flow cell and FIG. 16 shows a cross-sectional view of a part of the flow cell shown in FIG. 15. This flow cell is composed of a cylindrical cell body 1501 made of silica glass, three-way joints 1502 and 1503 provided with flow channels 1504 and 1505 and made of polyether ether ketone resin, tubings 1506 and 1507 made of polyether ether ketone resin, and optical fibers 1508 and 1509 made of silica glass that can introduce the light to be measured into the optical path inside the cell body 1501. After the cell body 1501 and the optical fibers 1508 and 1509 are modified with a hydrolyzable silicon compound 1510 via dip coating, the cylindrical tube, the optical fibers, the polyether ether ketone resin tubing, and the three-way joint are brought into contact with each other. Heating wires capable of covering areas surrounding the contact planes between each of the cylindrical tube, the optical fibers, and the polyether ether ketone resin tubings and the three-way joints are provided and the structure is heated to a temperature equivalent to or higher than the melting point of the polyether ether ketone resin. Thus, components are integrated with each other. This flow cell structure has an optical waveguide path in a liquid analyzer, and it is mainly used for absorbance and fluorescence analyses. An inner diameter of a cylindrical cell tube is preferably 0.01 mm to 1 mm and a cylindrical tube length is preferably 0.5 mm to 1000 mm.

In general, a flow cell for a microchip that is extensively used for analytical chemistry is made of a silica glass substrate or silicone resin that can be bonded to each other. In order to produce a connection for a microchip using silica glass a glass substrate and a polyether ether ketone resin, however, available techniques were limited to pressure bonding using a screw and the like. In addition, methods of bonding a flow cell to an external tubing that have actually been practiced in the past were limited to a method involving pressure bonding using a screw and the like. According to such conventional technique, disadvantageously, the number of components was large and pressure resistance was as low as about several MPa. However, the composite structure provided with a flow channel according to the present invention is capable of overcoming the disadvantages described above, and it is preferably used as a flow cell for a microchip.

Figure 17:
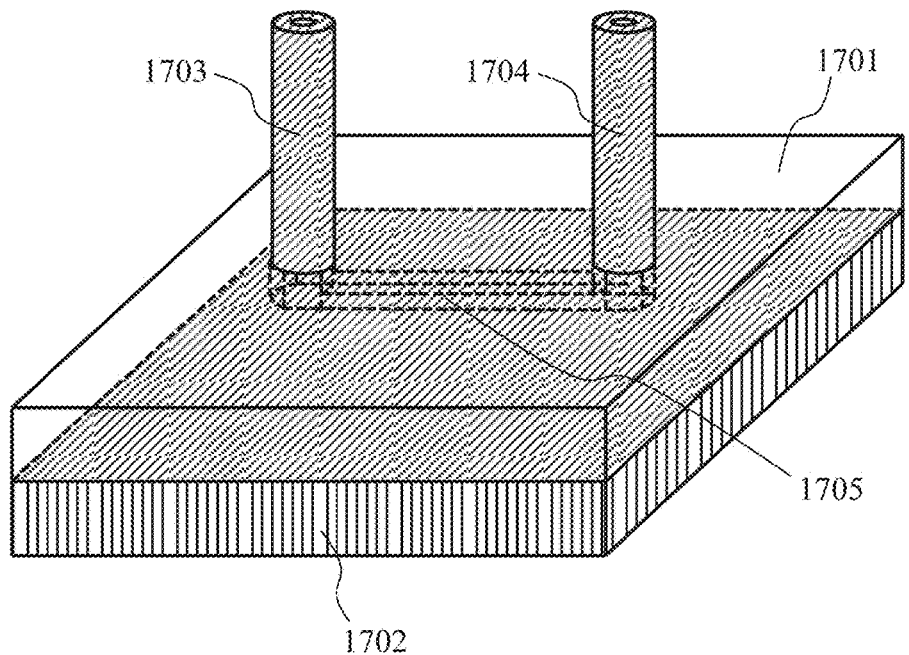
FIG. 17 shows a perspective view of the composite structure provided with a flow channel according to an embodiment of the present invention.
Figure 18:
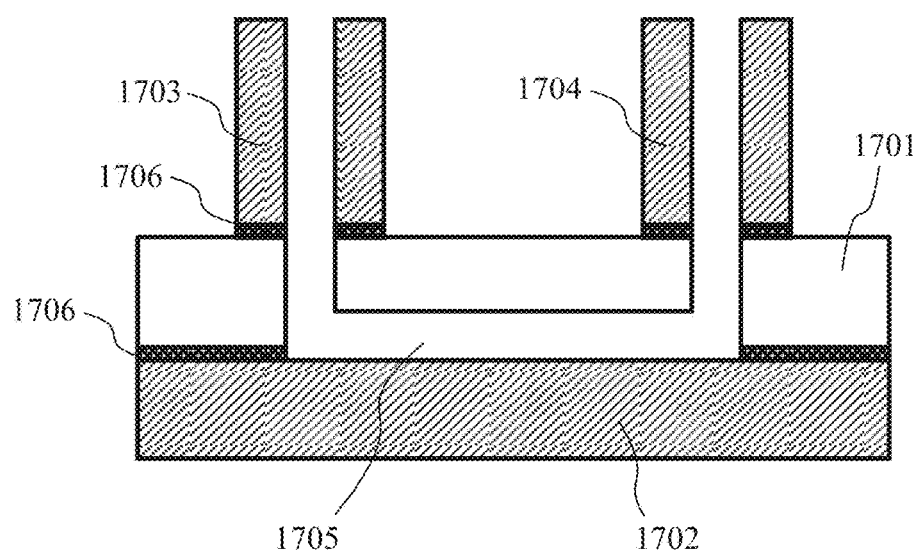
FIG. 18 shows a cross-sectional view of the composite structure provided with a flow channel according to an embodiment of the present invention.

FIG. 17 and FIG. 18 each show a flow cell for a microchip according to an embodiment of the present invention. FIG. 17 and FIG. 18 show a perspective view and a cross-sectional view of the same flow cell. This flow cell is composed of a first substrate 1701 made of silica glass, a second substrate 1702 made of polyether ether ketone resin, and tubings 1703 and 1704 made of polyether ether ketone resin. A flow channel 1705 connected to the tubings 1703 and 1704 is provided in advance inside the first substrate 1701. After the first substrate 1701 is modified with a hydrolyzable silicon compound 1706 via dip coating, the first substrate 1701 is brought into contact with the second substrate 1702. Thereafter, the contact plane between the first substrate 1701 and the second substrate 1702 is heated to a temperature equivalent to or higher than the melting point of the polyether ether ketone resin from the first substrate 1701 side using a plate electrically heated to a temperature equivalent to or higher than the melting point of the polyether ether ketone resin. The resultant is then naturally cooled to room temperature to allow the second substrate 1702 to resolidify.

Subsequently, a heating wire capable of thermal pressure bonding is provided in the vicinity of the contact plane between the first substrate 1701 and the tubing 1703 or 1704 in the same manner as that shown in FIG. 11, the contact plane is heated to a temperature equivalent to or higher than the melting point of the polyether ether ketone resin while pressing the heating wire against the tubing 1703 or 1704, and the polyether ether ketone resin tubing is then naturally cooled to resolidify. Thus, a flow cell for a microchip comprising silica glass and polyether ether ketone resin tightly adhering to each other can be produced.

The width of the flow channel 1705 according to this embodiment is preferably 1 μm to 1 mm and the height of the flow channel is preferably 1 μm to 1 mm. Materials constituting the substrates of the structure may be replaced with each other. In such a case, tubing is preferably made of silica glass. While a cross section of the flow channel is in a rectangular form in this embodiment, a cross section may be in a circular, elliptical, or polygonal form.

Figure 19:
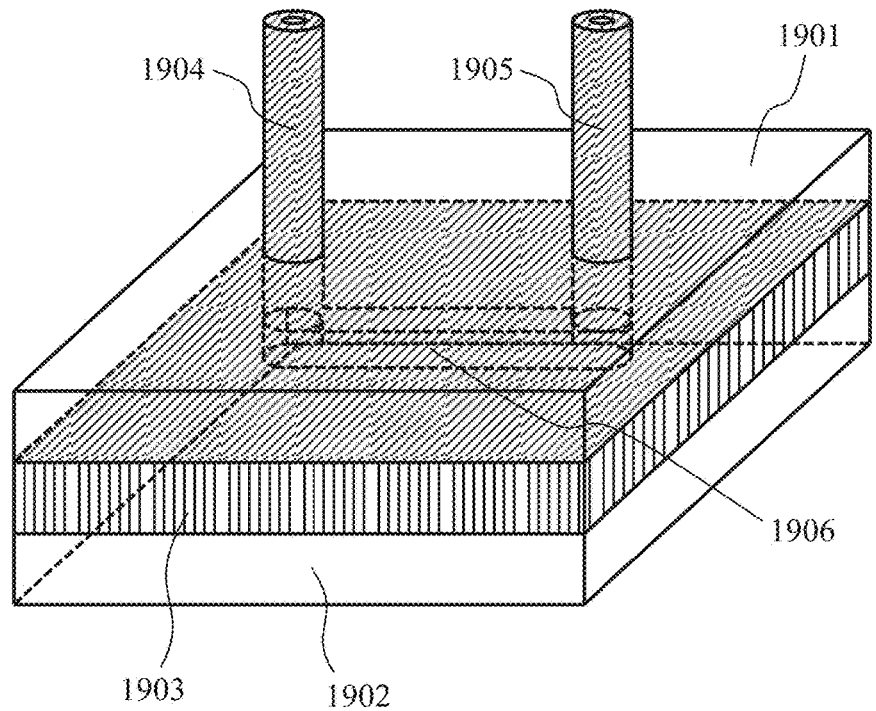
FIG. 19 shows a perspective view of the composite structure provided with a flow channel according to an embodiment of the present invention.
Figure 20:
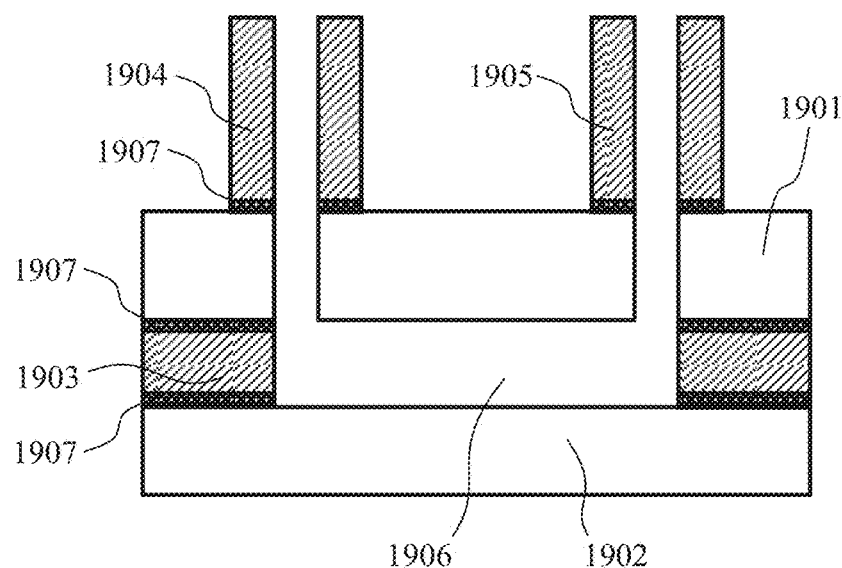
FIG. 20 shows a cross-sectional view of the composite structure provided with a flow channel according to an embodiment of the present invention.

A flow cell for photometric analysis may be a composite structure comprising a glass substrate provided with holes to be connected to tubings, a polyether ether ketone resin substrate provided with a slot for a flow channel, and another glass substrate superposed on top of each other, and a polyether ether ketone resin tubing is connected thereto. FIG. 19 and FIG. 20 each show a flow cell according to such embodiment. FIG. 19 and FIG. 20 show a perspective view and a cross-sectional view of the same flow cell. This flow cell is composed of first substrates 1901 and 1902 made of silica glass, a second substrate 1903 made of polyether ether ketone resin, and tubings 1904 and 1905 made of polyether ether ketone resin. In the same procedure as that shown in FIG. 17, a silica glass surface is modified with the hydrolyzable silicon compound 1907, and a flow cell for a microchip comprising silica glass and polyether ether ketone resin tightly adhering to each other can be produced. Thus, light can permeate the flow cell, which enables absorbance analysis and fluorescence analysis.

While embodiments in which the number of components was minimized were described above, for example, an electric heating member may constitute a part of a composite structure provided with a flow channel.

In order to confirm the effects of improved adhesion strength according to the present invention, the adhesion plane between the silica glass plate and the polyether ether ketone resin plate according to a conventional technique was compared with that according to the present invention. As a result, formation of interference fringes was observed in the conventional technique, but formation of interference fringes was not observed in the present invention. This indicates that irregularities on a scale comparable with light wavelength were formed at the contact plane due to the low affinity between silica glass and polyether ether ketone resin according to a conventional technique; however, such irregularities disappeared because of the improved affinity between the substrates according to the present invention. When shear stress was applied to a region between the substrates, a higher yield stress was exhibited by the present invention than by the conventional technique. In addition, the adhesion plane between the silica glass plate and the polyether ether ketone resin plate was broken according to the conventional technique; however, a silica glass bulk body was broken instead of the adhesion plane according to the present invention. The results indicate that the adhesion strength is not improved as a result of pressure bonding, but rather that it is improved by chemical bonding and anchor effects.

Table 1 shows pressure resistance of the composite structure determined when various conditions for dehydrating the hydrolyzable silicon compound after it had modified the silica glass surface were examined.

TABLE 1

| Dehydration conditions | Pressure resistance |
|---|---|
| 150° C., 20 minutes | x (<0.1 MPa) |
| 150° C., 10 minutes | Δ (5 MPa) |
| 150° C., 1 minute | ○ (≥20 MPa) |
| 28° C., 24 hours | ○ (≥20 MPa) |
| 28° C., 4 hours | ○ (≥20 MPa) |
| 28° C., 1 minute | ○ (≥20 MPa) |

Table 1 demonstrates that pressure resistance tends to decrease as the dehydration temperature is increased and the period of dehydration is prolonged. It is considered that such results are attained because hydrolysis of the hydrolyzable silicon compound advances more as the dehydration temperature is increased and the period of dehydration is prolonged, and the frequency for chemical bonding thereof to the polyether ether ketone resin lowers. Thus, the effects of the present invention are understood as being derived from adhesion strength that is improved via chemical bonding. Accordingly, the period during which the hydrolyzable silicon compound is allowed to stand after it is applied to the silica glass substrate surface and the remaining solvent is allowed to evaporate is preferably shorter.

Hereafter, the experimental examples verifying the effects according to the present invention are examined.

A polyether ether ketone resin tubing having an inner diameter of 0.7 mm, an outer diameter of 1.6 mm, and a length of 100 mm and a silica glass tubing having an inner diameter of 0.5 mm, an outer diameter of 0.6 mm, and a length of 100 mm were prepared. With the use of an isopropanol solution comprising 1% by weight of 1,000- to 2,000-mers of tetraethoxysilane dissolved therein, a silica glass surface was modified with a hydrolyzable silicon compound via dip coating. Thereafter, as shown in FIG. 1 and FIG. 2, the silica glass tubing was inserted to a depth of 10 mm into a polyether ether ketone resin tubing, an area in the vicinity of a contact region between the silica glass tubing and the polyether ether ketone resin tubing was heated to 400° C. using a heating wire in a shape capable of covering the contact plane, and the resultant was naturally cooled to room temperature to produce a composite tubing. For the purpose of comparison, a composite tubing in which tubings were adhered to each other was produced in the manner as described above while refraining from using the hydrolyzable silicon compound in accordance with a conventional technique. When melting polyether ether ketone resin, two tubings were subjected to thermal pressure bonding using a circular metal plate made of stainless steel.

Figure 21:
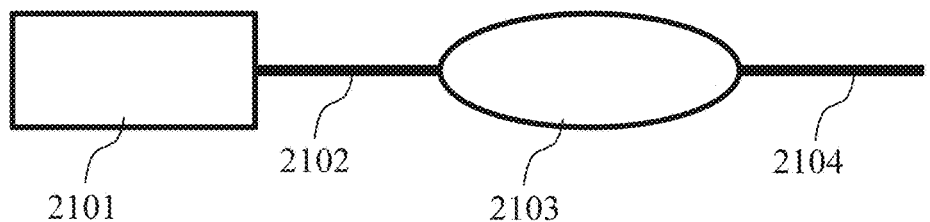
FIG. 21 schematically shows an experimentation system of the pressure resistance test according to the present invention.
Figure 22:
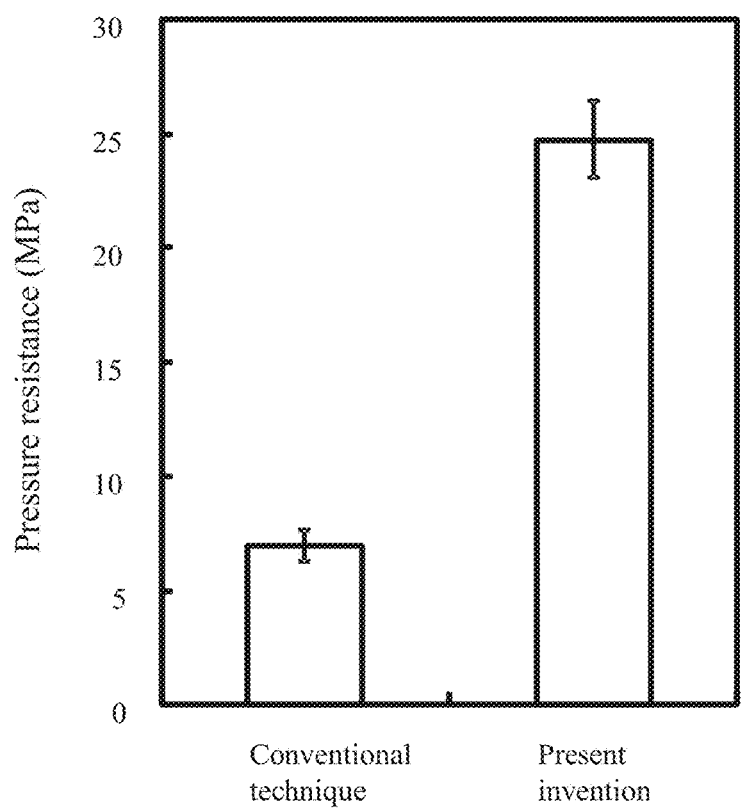
FIG. 22 shows the results of the pressure resistance tests of the composite structure provided with a flow channel according to a conventional technique and according to the present invention.

For the pressure resistance test, a pump capable of delivering liquid at a high pressure, such as a pump 2101 for a liquid chromatography apparatus, and an acetonitrile solution were prepared, and the experimentation system shown in FIG. 21 was connected. A tubing 2102, a composite body 2103 provided with a flow channel, and a tubing 2104 for pressure application are connected to the pump 2101. A stainless steel tubing with an inner diameter of 1 mm was used as the tubing 2102, so that the pressure could be suppressed to an ignorable level, and a stainless steel tubing with an inner diameter of 0.1 mm was used as the tubing 2104, so that pressure could be applied thereto. The liquid delivery pressure at which liquid leakage occurs was designated as the pressure resistance level, and the conventional technique was compared with the present invention. As a result, as shown in FIG. 22, liquid leakage was observed at a liquid delivery pressure of 6 MPa on average according to the conventional technique, and liquid leakage was observed at a liquid delivery pressure of 25 MPa on average according to the present invention. Thus, significant improvement in pressure resistance according to the present invention was confirmed. According to the present invention, a fissure was generated in the bulk body of the polyether ether ketone resin tubing instead of the plane on which two tubings were bonded to each other, and liquid leakage occurred therein. Such results also verify the improved adhesion strength because of chemical bonding and anchor effects.

As another embodiment, two silica glass window materials with a diameter of 10 mm and a cell body made of polyether ether ketone resin provided with a hole for a flow channel with a diameter of 0.5 mm and a hole for an optical path with a diameter of 0.9 mm and a length of 10 mm were prepared, and the window materials were modified with a hydrolyzable silicon compound with the isopropanol solution via dip coating. Thereafter, the cell body was sandwiched with the window materials, the contact planes between the cell body and the window materials were heated to 400° C. through the window material using plates heated to 400° C., and the resultant was naturally cooled to room temperature. A tubing with an inner diameter of 0.1 mm comprising a glass capillary coated with polyether ether ketone resin was provided at the inlet and the outlet of the flow channel of the cell body, and an area in the vicinity of the cell body and the tubing was heated to 400° C. using a heating wire in a shape capable of covering the contact planes. Thereafter, the resultant was naturally cooled to room temperature so as to produce a flow cell shown in FIG. 11. For a comparison, a flow cell shown in FIG. 11 was produced using a cell body with dimensions and a configuration identical to those of the cell body described above, which is made of stainless steel, by subjecting the window materials and the cell body to a mechanical fastening system according to a conventional technique involving the use of 12 components, such as ferrules, nuts, and O rings.

As a result of the pressure resistance test performed using the experimental system shown in FIG. 21, pressure resistance according to the conventional technique was found to be 12 MPa on average, and pressure resistance according to the present invention was found to be 25 MPa on average. Thus, the improvements in terms of the number of components reduced and pressure resistance according to the present invention were confirmed.

As a further embodiment, a cell body comprising a silica glass capillary having an inner diameter of 0.1 mm, an outer diameter of 0.35 mm, and a length of 3 mm, a two-way joint made of polyether ether ketone resin provided with a 0.4-mm hole for a flow channel, and a tubing having an inner diameter of 0.1 mm composed of a glass capillary coated with polyether ether ketone resin were prepared. The cell body surface was modified with the isopropanol solution. Thereafter, the cell body, the two-way joint, and the tubing were positioned as shown in FIG. 12, and heating wires capable of covering the contact planes were positioned in the vicinities of the regions in which the components described above were connected to each other, so as to heat the structure to 400° C. The structure was naturally cooled to room temperature to produce a flow cell shown in FIG. 12. For a comparison, a flow cell was produced in the manner as described above while refraining from using a hydrolyzable silicon compound in accordance with a conventional technique. As a flow cell shown in FIG. 15, also, a cell body comprising a silica glass capillary having an inner diameter of 0.5 mm, an outer diameter of 0.6 mm, and a length of 10 mm, a quartz optical fiber having a core diameter of 0.4 mm, a clad diameter of 0.44 mm, and a length of 45 mm, a three-way joint made of polyether ether ketone resin provided with a 0.7-mm hole for a flow channel, and a commercially available tubing having an inner diameter of 0.1 mm composed of a polyimide-coated glass capillary coated with polyether ether ketone resin were prepared, and the cell body surface and the optical fiber surface were modified with the isopropanol solution. Thereafter, the cell body, the optical fiber, the three-way joint, and the tubing were positioned as shown in FIG. 15, and heating wires capable of covering the contact planes were positioned in the vicinities of the regions in which the components described above were connected to each other, so as to heat the structure to 400° C. The structure was naturally cooled to room temperature to produce a flow cell shown in FIG. 15. For a comparison, a flow cell was produced in the manner as described above while refraining from using a hydrolyzable silicon compound in accordance with a conventional technique.

Figure 23:
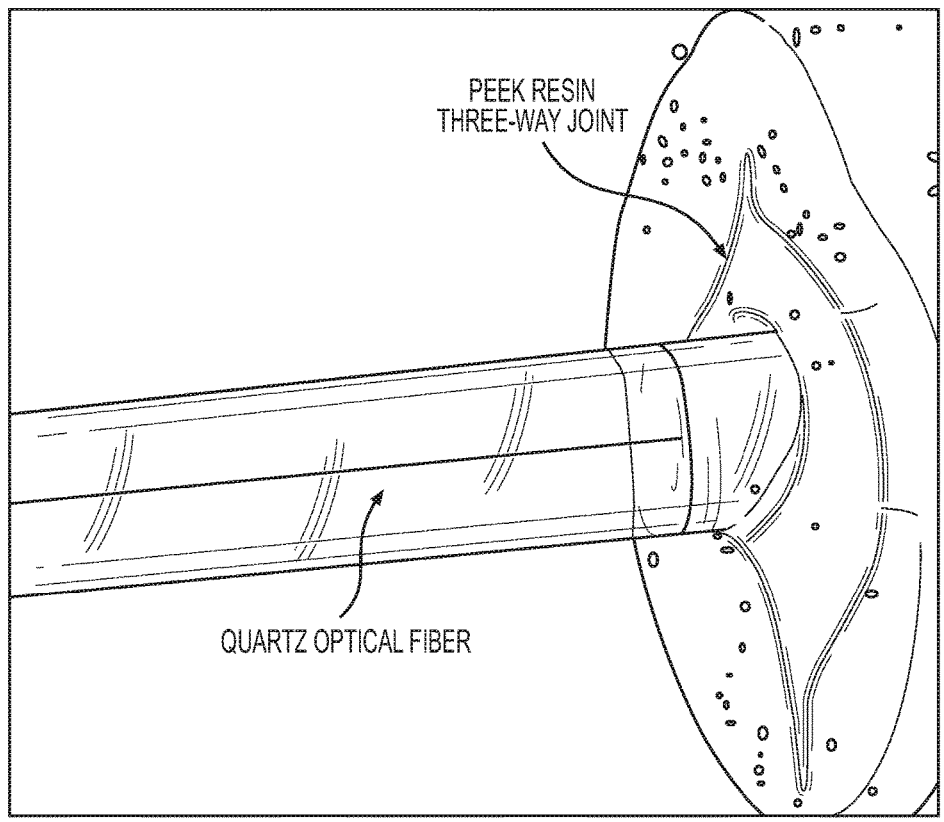
FIG. 23 shows the exterior of the composite structure provided with a flow channel according to an embodiment of the present invention.
Figure 24:
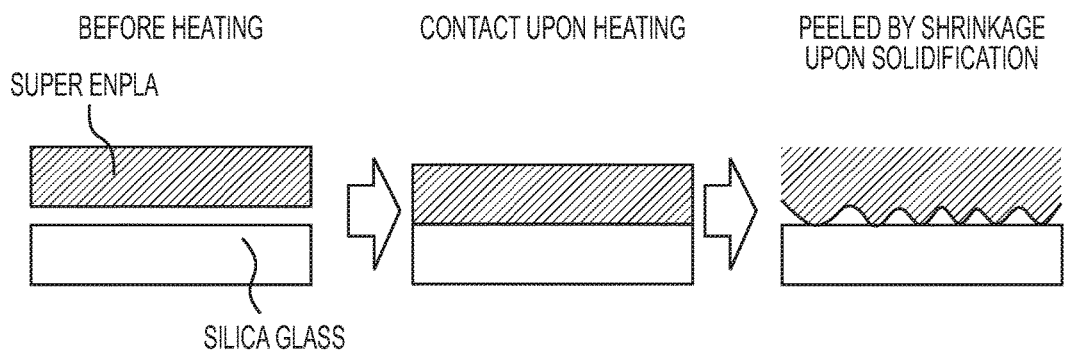
FIG. 24 illustrates the problem of bonding between silica glass and super enpla in a planar form according to a conventional technique.
Figure 25:
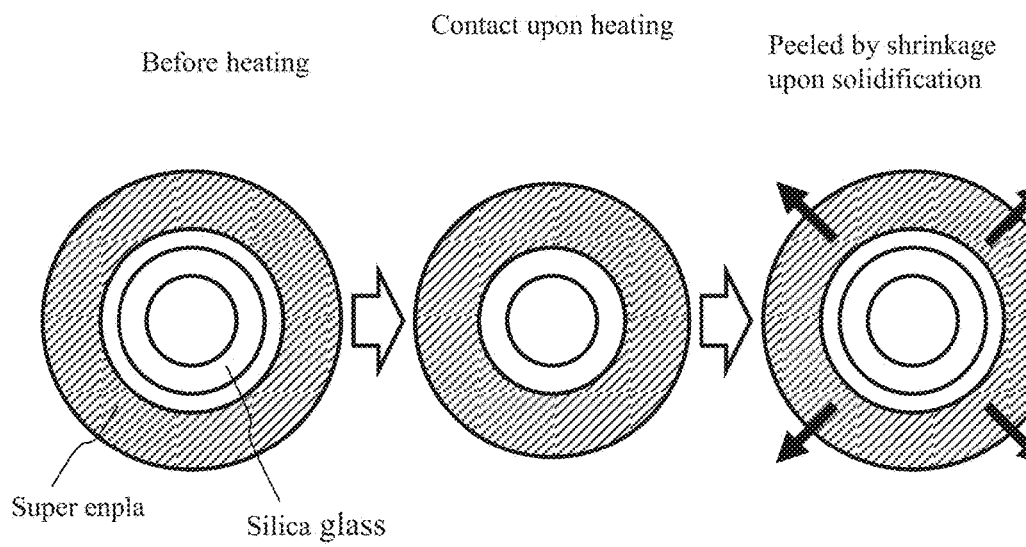
FIG. 25 illustrates the problem of bonding between silica glass and super enpla in a cylindrical form according to a conventional technique.
Figure 26:
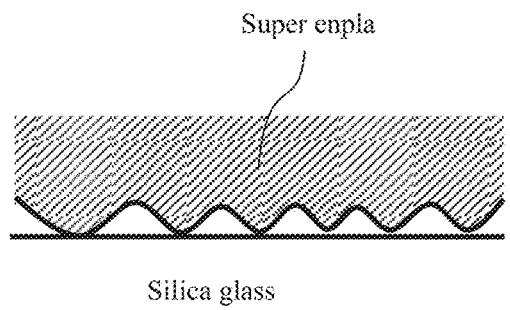
FIG. 26 illustrates the problem of bonding between silica glass and super enpla in a planar form according to another conventional technique.
Figure 27:
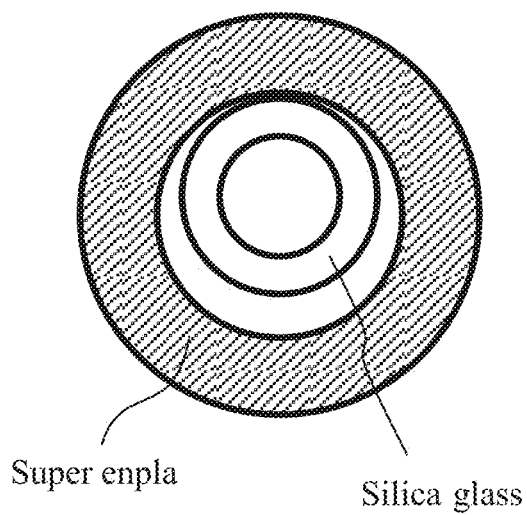
FIG. 27 illustrates the problem of bonding between silica glass and super enpla in a cylindrical form according to another conventional technique.

As a result of the pressure resistance test of the flow cell, pressure resistance of the flow cell according to the conventional technique was found to be 5 MPa on average, and pressure resistance of the flow cell according to the present invention was found to be 25 MPa on average. At the end of the region in which the three-way joint is connected to the optical fiber in the flow cell according to the present invention, as shown in FIG. 23, a configuration such that the polyether ether ketone resin wets the silica glass, and more specifically, a configuration such that the polyether ether ketone resin forms a convex configuration with respect to the quartz optical fibers, was observed.

Finally, embodiments of a flow cell for a microchip are described. Two silica glass plates (thickness: 1 mm; 5 mm×5 mm) were prepared, and one of the silica glass plates was provided with two 0.5-mm holes at an interval of 2 mm. The polyether ether ketone resin plate (thickness: 1 mm; 5 mm×5 mm) was provided with a hole for a flow channel (0.5 mm×2 mm). After the silica glass plates were modified with the hydrolyzable silicon compound using the isopropanol solution, the polyether ether ketone resin plate was sandwiched with the silica glass plates, the silica glass plates were further sandwiched with the plates heated to 400° C., and the areas of contact between the silica glass and the polyether ether ketone resin were heated to 400° C. After the structure had naturally cooled to room temperature, a tubing with an inner diameter of 0.5 mm composed of a glass capillary coated with polyether ether ketone resin was positioned within a hole provided on the silica glass. The structure was heated to 400° C. using a heating wire and then naturally cooled to room temperature to produce a flow cell shown in FIG. 19. For a comparison, a flow cell in the same configuration was produced using commercially available pressure bonding components.

As a result of the pressure resistance test performed using the experimental system shown in FIG. 21, pressure resistance according to the conventional technique was found to be 3 MPa on average, and pressure resistance according to the present invention was found to be 23 MPa on average. Thus, the present invention is effective for a flow cell for a microchip.

In the embodiments described above, it was confirmed that pressure resistance attained via electromagnetic induction heating would be substantially the same as that attained via electrical heating.

It should be noted that the present invention is not limited to the embodiments described above and various modifications thereof are within the scope of the present invention. For example, the embodiments above are described in detail to clearly explain the present invention, and the present invention is not limited to embodiments comprising all the constituents described herein. A part of a constitution according to a particular embodiment can be replaced with a constitution according to another embodiment, and a constitution according to a particular embodiment can be added to a constitution according to another embodiment. In addition, a part of a constitution according to an embodiment can be modified with another constitution through addition, deletion, or replacement.

DESCRIPTION OF NUMERAL REFERENCES

301: First cylindrical tube
302: Second cylindrical tube
801, 1201, 1401, 1501: Cell body
802, 803: Window material
804, 1204, 1205, 1404, 1405, 1504, 1505, 1705, 1906: Flow channel
805, 1208, 1510, 1706, 1907: Hydrolyzable silicon compound
806, 807: Heating plate
808, 809, 1206, 1207, 1406, 1407, 1506, 1507, 1703, 1704, 1904, 1905: Tubing
1202, 1203, 1401, 1402: Two-way joint
1502, 1503: Three-way joint
1508, 1509: Optical fiber
1701, 1901, 1902: Silica glass substrate
1702, 1903: Resin substrate

The invention claimed is:

1. A method for producing a composite structure comprising a flow channel and constituted of a glass substrate and a resin substrate comprising:
   a step of modifying a glass substrate surface with a hydrolyzable silicon compound;
   a step of bringing the glass substrate into contact with the resin substrate selected from polyether ether ketone resin, polyphenylene sulfide resin or polyamide resin; and
   a step of heating the contact surface between the glass substrate and the resin substrate to a temperature from the melting point to the pyrolysis temperature of the resin substrate, allowing the glass substrate to adhere to the resin substrate by eliminating gaps therebetween, and causing chemical bonding between the glass substrate and the resin substrate via the hydrolyzable silicon compound.

2. The method of production according to claim 1, wherein the glass substrate is synthetic silica glass, fused-silica glass, borosilicate glass, or soda glass.

3. The method of production according to claim 1, wherein the hydrolyzable silicon compound comprises an alkoxy group.

4. The method of production according to claim 1, wherein the glass substrate surface is modified with the hydrolyzable silicon compound via wet coating using a solution.

5. The method of production according to claim 1, wherein the flow channel provided in the composite structure is a flow cell for a liquid analyzer.

6. The method of production according to claim 1, wherein, after the contact surface between the glass substrate and the resin substrate is heated to a temperature from the melting point to the pyrolysis temperature of the resin substrate so that the glass substrate is allowed to adhere to the resin substrate by eliminating gaps therebetween, when the resin substrate is resolidified, in the contact surface between the glass substrate and the resin substrate, while the resin substrate is shrunk so that an angle formed by an end plane of a region in which the resin substrate is bonded to the glass substrate with respect to the contact surface is from 0 degrees to 90 degrees, chemical binding is caused between the glass substrate and the resin substrate via the hydrolyzable silicon compound.

7. The method of production according to claim 1, wherein the flow channel constituted of the glass substrate chemically bonded with the resin substrate has a pressure resistance greater than or equal to 20 MPa.

8. The method of production according to claim 1, wherein the glass substrate is a cylindrical glass tube and the resin substrate is a cylindrical resin tube, and wherein the glass substrate is brought into contact with the resin substrate by placing the cylindrical glass tube within the cylindrical resin tube.

9. A flow cell for a liquid analyzer comprising:
a flow channel constituted of a glass substrate adhered to a resin substrate via chemical bonding of a hydrolyzable silicon compound,
wherein the resin substrate is selected from polyether ether ketone resin, polyphenylene sulfide resin or polyamide resin,
wherein the glass substrate is in contact with the resin substrate via the hydrolyzable silicon compound and the resin substrate is melted on the glass substrate.

10. The flow cell according to claim 9, wherein the glass substrate is synthetic silica glass, fused-silica glass, borosilicate glass, or soda glass.

11. The flow cell according to claim 9, wherein the flow channel constituted of the glass substrate chemically bonded with the resin substrate has a pressure resistance greater than or equal to 20 MPa.

12. The flow cell according to claim 9, wherein the glass substrate is a cylindrical glass tube and the resin substrate is a cylindrical resin tube, and
wherein the cylindrical glass tube is disposed within the cylindrical resin tube.

* * * * *